(12) United States Patent
Field et al.

(10) Patent No.: US 8,029,739 B2
(45) Date of Patent: Oct. 4, 2011

(54) ULTRAVIOLET SANITATION DEVICE

(75) Inventors: Bruce F. Field, Golden Valley, MN (US); Joseph L. Pouliot, Elk River, MN (US)

(73) Assignee: Tennant Company, Minneapolis, MN (US)

( * ) Notice: Subject to any disclaimer, the term of this patent is extended or adjusted under 35 U.S.C. 154(b) by 1784 days.

(21) Appl. No.: 10/909,070

(22) Filed: Jul. 30, 2004

(65) Prior Publication Data
US 2005/0022844 A1     Feb. 3, 2005

Related U.S. Application Data

(60) Provisional application No. 60/491,181, filed on Jul. 30, 2003.

(51) Int. Cl.
- *A61L 2/00* (2006.01)
- *A61L 9/00* (2006.01)
- *A61K 39/02* (2006.01)
- *B01J 19/00* (2006.01)

(52) U.S. Cl. .......... 422/292; 422/243; 422/291; 422/22; 422/24

(58) Field of Classification Search .................. 422/291, 422/292, 243, 22, 24
See application file for complete search history.

(56) References Cited

U.S. PATENT DOCUMENTS

| | | | |
|---|---|---|---|
| 3,938,212 A | 2/1976 | Krier et al. ................. | 15/50 |
| 3,942,218 A | 3/1976 | Krier et al. ................. | 15/340 |
| 3,979,789 A | 9/1976 | Peabody et al. ............. | 15/349 |
| 4,014,808 A | 3/1977 | Herpers, Jr. et al. ......... | 252/135 |
| 4,032,307 A | 6/1977 | Sommerfeld ............... | 55/96 |
| 4,037,289 A | 7/1977 | Dojan ...................... | 15/320 |
| D245,994 S | 10/1977 | Olson ...................... | D23/162 |
| 4,096,084 A | 6/1978 | Thomsen et al. ............ | 252/173 |
| 4,099,285 A | 7/1978 | Christensen et al. .......... | 15/83 |
| 4,138,756 A | 2/1979 | Krier et al. ................ | 15/83 |
| RE29,957 E | 4/1979 | Kasper .................... | 15/83 |
| 4,173,056 A | 11/1979 | Geyer ..................... | 15/320 |
| 4,194,263 A | 3/1980 | Herpers et al. ............. | 15/353 |
| 4,206,530 A | 6/1980 | Kroll et al. ................ | 15/340 |
| D257,845 S | 1/1981 | Peabody et al. ............ | D15/50 |
| 4,258,451 A | 3/1981 | Sommerfeld ............... | 15/352 |
| 4,262,382 A | 4/1981 | Brown et al. .............. | 15/49 |

(Continued)

FOREIGN PATENT DOCUMENTS

| | | |
|---|---|---|
| DE | 8807550 | 4/1990 |
| DE | 19613758 | 10/1997 |
| GB | 910229 | * 11/1962 |
| GB | 2277251 | 10/1994 |
| WO | WO 98/27891 | 7/1998 |

OTHER PUBLICATIONS

Notification of Transmittal of the International Search Report and the Written Opinion of the International Searching Authority for International Patent Application No. PCT/US2004/024729, filed Jul. 30, 2004; date of mailing: Jan. 24, 2005.

(Continued)

*Primary Examiner* — Sean E Conley
*Assistant Examiner* — Regina Yoo
(74) *Attorney, Agent, or Firm* — Westman, Champlin & Kelly, P.A.

(57) ABSTRACT

A sanitation device includes a mobile body, a surface cleaning component, and a source of UV radiation. The surface cleaning component and the source of UV radiation are mounted to the mobile body, which is configured to travel over a surface. The surface cleaning component is configured to engage the surface and the source of UV radiation is configured to direct UV radiation to the surface.

7 Claims, 9 Drawing Sheets

U.S. PATENT DOCUMENTS

| | | | | |
|---|---|---|---|---|
| 4,295,244 A | 10/1981 | Herpers et al. | | 15/320 |
| 4,310,944 A | 1/1982 | Kroll et al. | | 15/346 |
| 4,320,556 A | 3/1982 | Kimzey et al. | | 15/347 |
| 4,334,335 A | 6/1982 | Brown et al. | | 15/319 |
| 4,345,353 A | 8/1982 | Sommerfeld | | 15/349 |
| 4,346,494 A | 8/1982 | Peabody et al. | | 15/179 |
| 4,348,783 A | 9/1982 | Swanson et al. | | 15/320 |
| 4,355,435 A | 10/1982 | Kimzey et al. | | 15/347 |
| 4,365,189 A | 12/1982 | Hawkins et al. | | 318/284 |
| D267,824 S | 2/1983 | Mannelly | | D32/16 |
| 4,373,227 A | 2/1983 | Kimzey et al. | | 15/347 |
| 4,377,017 A | 3/1983 | Herpers et al. | | 15/320 |
| 4,378,855 A | 4/1983 | Haub et al. | | 180/65 |
| 4,393,538 A | 7/1983 | Olson | | 15/320 |
| D273,620 S | 4/1984 | Kimzey et al. | | D32/16 |
| D273,621 S | 4/1984 | Haub et al. | | D32/16 |
| D273,622 S | 4/1984 | Brown et al. | | D32/16 |
| 4,457,036 A | 7/1984 | Carlson et al. | | 15/49 |
| 4,557,739 A | 12/1985 | Fortman et al. | | 55/320 |
| 4,571,771 A | 2/1986 | Worwa | | 15/319 |
| 4,580,313 A | 4/1986 | Blehert | | 15/349 |
| 4,586,208 A | 5/1986 | Trevarthen | | 8/158 |
| 4,608,086 A | 8/1986 | Dodge | | 106/12 |
| 4,615,070 A | 10/1986 | Frederick et al. | | 15/339 |
| 4,624,026 A | 11/1986 | Olson et al. | | 15/340 |
| 4,634,403 A | 1/1987 | Peabody et al. | | 474/1 |
| 4,675,935 A | 6/1987 | Kasper et al. | | 15/319 |
| 4,679,271 A | 7/1987 | Field et al. | | 15/49 |
| 4,709,771 A | 12/1987 | Basham et al. | | 180/6.5 |
| 4,729,141 A | 3/1988 | Berg et al. | | 15/49 |
| 4,757,566 A | 7/1988 | Field et al. | | 15/49 |
| 4,768,311 A | 9/1988 | Olson | | 51/174 |
| 4,805,256 A | 2/1989 | Mason et al. | | 15/320 |
| 4,805,258 A | 2/1989 | Sitarski et al. | | 15/385 |
| 4,817,233 A | 4/1989 | Waldhauser | | 15/320 |
| 4,819,676 A | 4/1989 | Blehert et al. | | 134/21 |
| 4,866,804 A | 9/1989 | Masbruch et al. | | 15/49 |
| 4,877,964 A | 10/1989 | Tanaka | | 250/455.1 |
| 4,881,288 A | 11/1989 | May et al. | | 15/98 |
| 4,907,316 A * | 3/1990 | Kurz | | 15/319 |
| 4,919,117 A * | 4/1990 | Muchisky et al. | | 601/114 |
| 4,967,064 A | 10/1990 | Field et al. | | 250/203.2 |
| 4,986,378 A | 1/1991 | Kasper | | 180/6.48 |
| 4,996,468 A | 2/1991 | Field et al. | | 318/587 |
| 5,006,694 A * | 4/1991 | Handke et al. | | 219/121.6 |
| 5,013,333 A | 5/1991 | Beaufoy et al. | | 55/21 |
| 5,016,310 A | 5/1991 | Geyer et al. | | 15/49.1 |
| 5,044,043 A | 9/1991 | Basham et al. | | 15/319 |
| 5,045,118 A | 9/1991 | Mason et al. | | 134/21 |
| 5,064,010 A | 11/1991 | Masbruch et al. | | 180/6.5 |
| 5,068,260 A * | 11/1991 | Noguchi | | 522/31 |
| 5,088,149 A | 2/1992 | Berg et al. | | 15/322 |
| 5,093,955 A | 3/1992 | Blehert et al. | | 15/320 |
| RE33,926 E | 5/1992 | Waldhauser | | 15/320 |
| 5,212,848 A | 5/1993 | Geyer | | 15/401 |
| 5,231,725 A | 8/1993 | Hennessey et al. | | 15/83 |
| 5,244,003 A | 9/1993 | Boomgaarden | | 137/1 |
| 5,254,146 A | 10/1993 | Beaufoy | | 55/320 |
| 5,276,933 A | 1/1994 | Hennessey et al. | | 15/83 |
| 5,295,277 A | 3/1994 | Koenigs et al. | | 15/83 |
| 5,300,097 A * | 4/1994 | Lerner et al. | | 607/93 |
| 5,303,448 A | 4/1994 | Hennessey et al. | | 15/340.3 |
| 5,319,828 A | 6/1994 | Waldhauser et al. | | 15/320 |
| RE35,033 E | 9/1995 | Waldhauser | | 15/320 |
| 5,455,985 A | 10/1995 | Hamline et al. | | 15/4.01 |
| 5,483,718 A | 1/1996 | Blehert et al. | | 15/50.3 |
| 5,515,568 A | 5/1996 | Larson et al. | | 15/50.3 |
| 5,566,422 A | 10/1996 | Geyer | | 15/320 |
| 5,647,093 A | 7/1997 | Engel et al. | | 15/352 |
| 5,659,921 A | 8/1997 | Narayan | | 15/349 |
| 5,711,775 A | 1/1998 | Field et al. | | 55/273 |
| 5,829,094 A | 11/1998 | Field et al. | | 15/352 |
| 5,884,353 A | 3/1999 | Berg et al. | | 15/83 |
| 5,893,189 A | 4/1999 | D'Costa | | 15/83 |
| 5,901,407 A | 5/1999 | Boomgaarden | | 15/320 |
| 5,940,928 A | 8/1999 | Erko | | 15/319 |
| 5,940,929 A | 8/1999 | Berg | | 15/334 |
| 5,943,724 A | 8/1999 | Erko et al. | | 15/49.1 |
| 5,943,730 A | 8/1999 | Boomgaarden | | 15/320 |
| 5,958,336 A | 9/1999 | Duarte | | 422/24 |
| 5,967,747 A | 10/1999 | Burke et al. | | 415/206 |
| 5,983,447 A | 11/1999 | Boomgaarden | | 15/354 |
| 5,991,953 A | 11/1999 | Durenberger et al. | | 15/83 |
| 5,996,173 A | 12/1999 | Engel et al. | | 15/352 |
| 5,996,174 A | 12/1999 | Boomgaarden et al. | | 15/354 |
| 6,003,186 A | 12/1999 | Larson | | 15/82 |
| 6,018,844 A | 2/2000 | Basham et al. | | 15/349 |
| 6,035,479 A | 3/2000 | Basham et al. | | 15/83 |
| 6,073,295 A | 6/2000 | Durenberger et al. | | 15/83 |
| 6,092,261 A | 7/2000 | Boomgaarden | | 15/323 |
| 6,096,383 A * | 8/2000 | Berg et al. | | 427/493 |
| 6,117,200 A | 9/2000 | Berg et al. | | 55/287 |
| 6,125,495 A | 10/2000 | Berg et al. | | 15/183 |
| 6,191,924 B1 | 2/2001 | Koester | | 360/260 |
| 6,192,542 B1 | 2/2001 | Frederick et al. | | 15/84 |
| 6,202,243 B1 | 3/2001 | Beaufoy et al. | | 15/49.1 |
| 6,239,442 B1 * | 5/2001 | Iimura | | 250/504 R |
| 6,245,392 B1 * | 6/2001 | Hillenbrand | | 427/498 |
| 6,249,926 B1 | 6/2001 | Wulff | | 15/50.1 |
| 6,254,625 B1 | 7/2001 | Rosenthal et al. | | 607/88 |
| 6,286,169 B1 | 9/2001 | D'Costa et al. | | 15/52.1 |
| 6,389,641 B1 | 5/2002 | Boomgaarden et al. | | 15/340.1 |
| 6,398,829 B1 | 6/2002 | Shinler et al. | | 55/317 |
| 6,421,870 B1 | 7/2002 | Basham et al. | | 15/83 |
| 6,425,958 B1 | 7/2002 | Giddings et al. | | 134/21 |
| 6,428,590 B1 | 8/2002 | Lehman et al. | | 55/334 |
| 6,436,540 B1 * | 8/2002 | Garcia et al. | | 428/423.1 |
| 6,449,793 B2 | 9/2002 | D'Costa et al. | | 15/52.1 |
| 6,468,350 B1 | 10/2002 | Hillenbrand | | 118/620 |
| 6,472,027 B1 | 10/2002 | Olson et al. | | 427/492 |
| 6,507,968 B1 | 1/2003 | Hansen | | 15/49.1 |
| 6,530,102 B1 | 3/2003 | Pierce et al. | | 15/52.1 |
| 6,533,871 B2 | 3/2003 | Zahuranec et al. | | 134/21 |
| 6,538,258 B1 * | 3/2003 | Rau et al. | | 250/504 R |
| 6,585,827 B2 | 7/2003 | Field et al. | | 134/6 |
| 6,586,172 B1 * | 7/2003 | Gunn et al. | | 435/2 |
| 6,602,018 B2 | 8/2003 | Feeny et al. | | 403/227 |
| 6,614,195 B2 | 9/2003 | Bushey et al. | | 318/135 |
| 6,618,888 B2 | 9/2003 | Joynt et al. | | 15/49.1 |
| 6,651,286 B2 | 11/2003 | Pierce | | 15/98 |
| 6,662,402 B2 | 12/2003 | Giddings et al. | | 15/320 |
| 6,662,600 B1 | 12/2003 | Field et al. | | 68/17 |
| D485,175 S | 1/2004 | Field et al. | | D9/432 |
| 6,671,925 B2 | 1/2004 | Field et al. | | 15/320 |
| 6,705,332 B2 | 3/2004 | Field et al. | | 134/102.1 |
| 6,735,811 B2 | 5/2004 | Field et al. | | 15/320 |
| 6,735,812 B2 | 5/2004 | Hekman et al. | | 15/320 |
| 6,742,219 B2 | 6/2004 | Lenzmeier et al. | | 15/345 |
| 6,802,098 B2 | 10/2004 | Geyer et al. | | 15/52.1 |
| 6,836,919 B2 | 1/2005 | Shinler | | 15/78 |
| 6,860,794 B1 * | 3/2005 | Palushi et al. | | 451/41 |
| 6,877,180 B2 | 4/2005 | Wilmo et al. | | 15/83 |
| 2001/0051230 A1 * | 12/2001 | Colton et al. | | 427/508 |
| 2003/0019071 A1 | 1/2003 | Field et al. | | 15/320 |
| 2003/0111713 A1 * | 6/2003 | Cheng | | 257/668 |
| 2003/0124339 A1 | 7/2003 | Field et al. | | 428/323 |
| 2003/0159308 A1 | 8/2003 | Field et al. | | 34/275 |
| 2004/0040102 A1 | 3/2004 | Field et al. | | 15/50.1 |
| 2004/0187895 A1 | 9/2004 | Field et al. | | 134/26 |
| 2004/0221407 A1 | 11/2004 | Field et al. | | 15/50.1 |

OTHER PUBLICATIONS

Communication in Cases for Which No Other Form is Available and International Search Report for International Application No. PCT/US2004/024729, filed Jul. 30, 2004; date of mailing: Jan. 24, 2005.

U.S. Appl. No. 11/125,764, filed May 10, 2005, Field et al.

Web page of Pen-Ray Product Selector Guide, UVP, "Product Selector", May 12, 1998.

"Sterilization of Ultraviolet Irradiation," by I.L. Shechmeister, Ph.D., pp. 106-122.

* cited by examiner

ULTRAVIOLET SANITATION DEVICE

The present application is based on and claims the benefit of U.S. provisional patent application Ser. No. 60/491,181, filed Jul. 30, 2003, which is incorporated herein by reference in its entirety.

FIELD OF THE INVENTION

The present invention is generally directed to a sanitation device and, more particularly, to a sanitation device that includes a source of ultraviolet (UV) radiation that is used to sanitize a surface. Additional embodiments of the present invention are directed to methods of sanitizing surfaces using the device.

BACKGROUND OF THE INVENTION

There are many different types of surface cleaners that are configured for cleaning various surfaces such as, for example, streets, hard floors, and carpet. Examples of such cleaning machines are disclosed in U.S. Pat. Nos. 6,162,542, 6,585,827, 6,671,925, 6,705,332, and 6,735,812, which are assigned to Tennant Company of Minneapolis, Minn. and are incorporated herein by reference in their entirety. Such surface cleaners can be configured as riding or towed-behind units that are typically power driven. The surface cleaners machines includes a surface cleaning component that engages the surface over which the machine travels. The cleaning components can include rotatable scrubbers, which are typically found on carpet cleaners and extractors and hard floor surface cleaners, and rotatable sweepers, which are typically found on street or floor sweepers, for example.

Although such surface cleaners may provide excellent results, some environments (e.g., hospitals, food processing plants, etc.) require additional efforts to be made to ensure sanitization of the surface being cleaned. In those instances, the surface cleaners can apply a chemical disinfectant to the surface. Unfortunately, such chemicals can be hazardous requiring the user to take safety precautions before handling the chemicals, and special care in their disposal. As a result, the use of such chemicals can be dangerous, time consuming, and expensive.

SUMMARY OF THE INVENTION

The present invention generally relates to a sanitation device for sanitizing surfaces. In accordance with one embodiment of the invention, the sanitization device includes a mobile body and a source of UV radiation. The source of UV radiation is mounted to the mobile body, which is configured to travel over a surface. The source of UV radiation is configured to direct UV radiation to the surface at a dosage of less than 60 mW/cm$^2$.

In accordance with another embodiment of the invention, the sanitization device includes a mobile body, a surface cleaning component, and a source of UV radiation. The surface cleaning component and the source of UV radiation are mounted to the mobile body, which is configured to travel over a surface. The surface cleaning component is configured to engage the surface and the source of UV radiation is configured to direct UV radiation to the surface.

In accordance with yet another embodiment of the invention, the sanitization device includes a housing, a source of UV radiation, and a sensor. The source of UV radiation is contained in the housing and positioned to transmit UV radiation through an opening in the housing. The sensor is configured to detect when the source is within a predetermined distance from a surface to be sanitized.

Additional embodiments of the present invention are directed to methods of using the above-identified sanitization devices to sanitize a surface.

Other features and benefits that characterize embodiments of the present invention will be apparent upon reading the following detailed description and review of the associated drawings.

DETAILED DESCRIPTION OF THE PREFERRED EMBODIMENTS

The present invention generally relates to a sanitization device that utilizes a source of UV radiation to provide a means for sanitizing a surface. As will be discussed below in greater detail, embodiments of the sanitization device include a source of UV radiation in combination with a mobile body, or a housing for handheld operation. Additional embodiments of the present invention relate to methods of sanitizing surfaces using the sanitization devices of the present invention.

UV radiation is generally identified as having three ranges: UV-A covering wavelengths of 315 nanometers (nm) and higher, UV-B covering wavelengths of 280-315 nm and UV-C covering wavelengths of 280 nm and lower. It has been determined that microorganisms can be inactivated by the UV radiation having wavelengths in the UV-C range, particularly wavelengths of 240-260 nm. UV radiation does not necessarily kill the target organisms, instead the radiation alters the cell DNA so that the organisms are sterilized. This process serves to inactivate the pathogen so that it cannot proliferate and cause disease, odor, and other problems.

Figure 1:
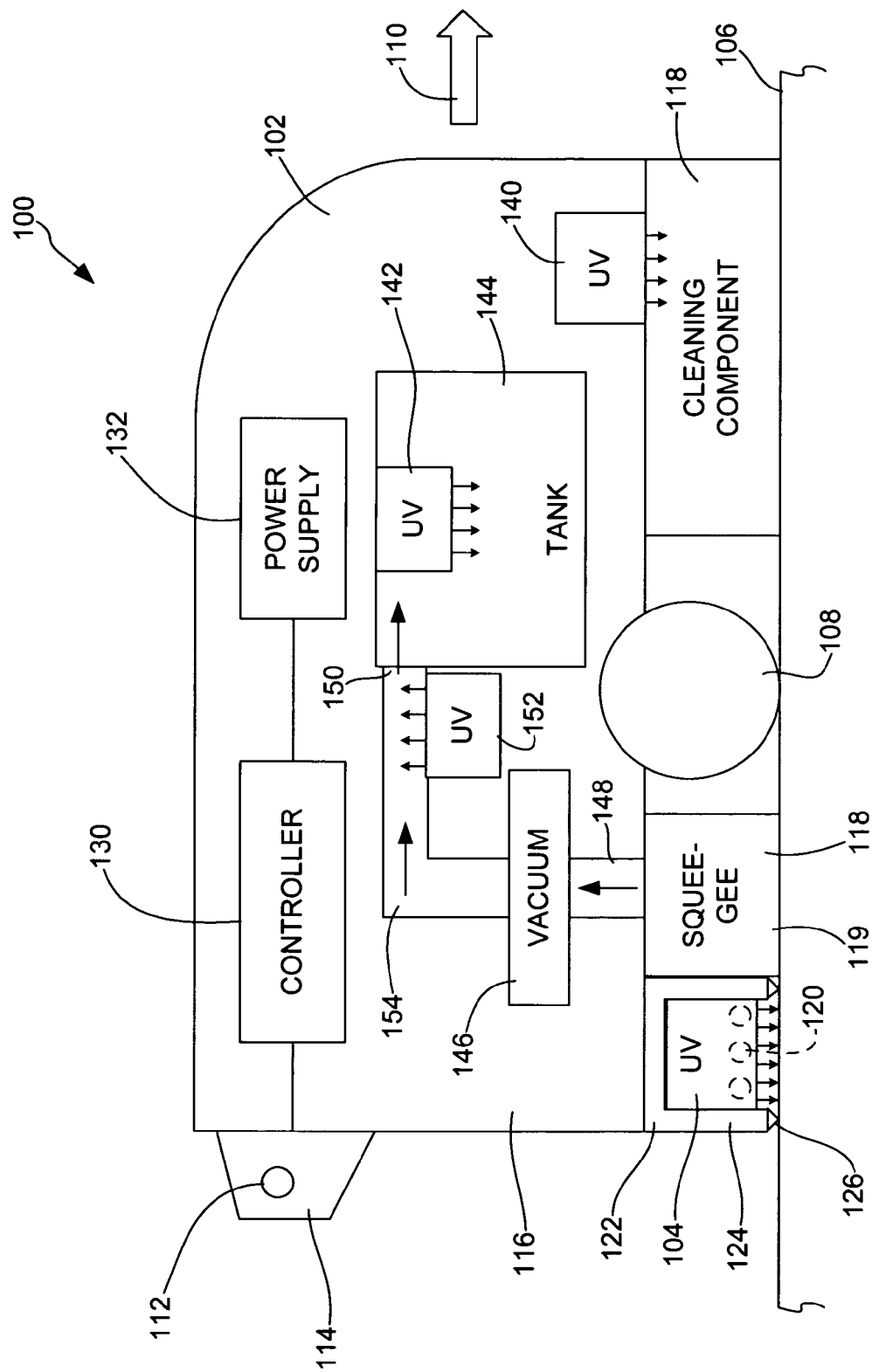
FIG. 1 is a simplified diagram of a sanitization device in accordance with embodiments of the invention.

FIG. 1 is a simplified diagram of a sanitization device 100 in accordance with embodiments of the invention. In general, the sanitization device 100 includes a mobile body 102 and a source of UV radiation 104 mounted to the mobile body 102. The mobile body 102 includes structures that are configured to travel across a surface 106 on wheels, such as wheels 108, rollers, slides (e.g., slidable feet) or other transport components that facilitate movement of the mobile body 102 across the surface 106.

The mobile body 102 may be configured for walk-behind operation (push or self-propelled), ride-on operation, or hand-held operation. Ride-on devices and self-propelled walk-behind devices may be advantageous where the operator desires to maintain a relatively constant speed, which can provide more control over the exposure surface 106 to UV radiation.

In the simplified example of the UV sanitization device 100 in FIG. 1, the mobile body 102 is depicted as a component of a walk-behind, push-powered machine configured to operate in a forward direction, as indicated by arrow 110. In this embodiment, an operator walks behind the device 100 and provides a pushing force to a handle 112 of an operator interface 114 at a rear end 116 to control the speed of the device 100 and the direction.

In accordance with one embodiment of the invention, sanitization device 100 can operate as a surface cleaner, such as a carpet cleaner or extractor, a hard floor surface cleaner or sweeper, a street sweeper, or other mobile surface cleaner. Accordingly, embodiments of sanitization device 100 include a surface cleaning component 118 configured to engage the surface 106 and perform a cleaning operation thereon. As will be discussed in greater detail below, embodiments of cleaning component 118 include rotatable scrubbers, rotatable sweepers, squeegees (e.g., squeegee 119), carpet cleaning extractors, fluid recovery devices, and other surface cleaning components.

The source of UV radiation 104 (hereinafter "source") is preferably configured to apply a substantially uniform dosage of UV radiation to the surface 106 across the width of the mobile body 102 of a sufficient magnitude to provide a degree of sanitization to the surface 106. Preferably, the dosage of radiation applied to the surface 106 by the source 104 is in a range of 10-60 mW/cm$^2$. The source 104 may include one or more UV lamps 120, or other suitable UV source. The UV lamps 120 are preferably mercury flood lamps having a ballast incorporated on the lamp (self-ballasted). Alternatively, the lamps 120 may be externally ballast driven. An optional cooling apparatus, such as a fan, may be provided to ensure sufficient cooling of the source 104. The wavelength of the UV radiation produced by the source 104 is preferably in the UV-C range, which is less than 280 nm. In accordance with one embodiment of the invention, the primary energy of the source 104 is at a wavelength that is within a range of 240-260 nm. One suitable source 104 is produce number 90-0012-01 manufactured by UVP, Inc. of Upland, Calif., which emits a mercury spectrum with the primary energy at a wavelength of 254 nm.

The source 104 is preferably supported above the surface 106 in a housing or mount 122. The source is preferably mounted to the mobile body at the rear end 116, as shown, but the source 104 could be mounted at other locations on the mobile body 102, such as along the sides and/or front of the mobile body.

The desired position of the source 104 relative to the surface 106 can vary depending upon the magnitude of the UV radiation produced thereby. Typically UV sources can be positioned within approximately 7.0 inches of the surface 106 and provide the desired dosage to the surface 106. The housing or mount 122 is preferably adjustably secured to the mobile body using bolts, latches, or other suitable components. Accordingly, the position of the source 104 can be adjusted through an adjustment of the housing or mount 122, or through a lifting mechanism.

Housing 122 preferably includes a bottom, through which UV radiation produced by the source 104 can be directed to the surface 106. Accordingly, the bottom of the housing 122 can be an open bottom, or covered with a UV-transparent material.

Shroud portions 124 of the housing 122 can cover portions of the source 104 that do not face the surface 106, to prevent undesirable leakage of the UV radiation from under housing 122. Accordingly, the shroud portions 124 of the housing 122 and the surface 106 preferably substantially enclose the source 104. One embodiment of the shroud portion 124 includes a flexible edge or skirt 126 that surrounds the bottom opening and extends toward the surface 106. The engagement of the surface 106 with a flexible edge or skirt 126 substantially contains the UV radiation beneath the housing 122. Additionally, the interior portion of the housing 122 or the shroud portions 124 can include reflective surfaces to direct the UV radiation produced by the source 104 toward the surface 106 to thereby improve efficiency.

A controller 130 operates to control power provided to the source 104 from either an onboard power supply 132, such as a battery or generator, or an external power supply received through a suitable cable. Electrical connections between the controller 130, the power supply 132, and the UV sources 104, are not shown in FIG. 1 to simplify the illustration. The power supply 132 may also be used to power electrical motors (not shown) of the device 100, which may be used to drive the cleaning component 118 and wheels 108 of the device 100.

The source 104 preferably requires very little power compared to UV sources that provide primary energy at higher wavelengths (i.e., above 280 nm). The effective power consumption of the source 104 is preferably less than 25 watts per inch of sanitized surface width.

Controller 130 preferably activates the source 104 in response to an input from the operator at the operator interface 114. In accordance with one embodiment of the invention, the controller 130 adjusts the power supplied to the source 104 by power supply 132 to substantially maintain a constant dosage of UV radiation, such as the preferred dosage of 10-60 mW/cm$^2$, to the surface 106 as the device 100 travels across the surface 106. Thus, controller 130 preferably adjusts the power supplied to the source 104 automatically in response to the speed at which the mobile body 102 travels over the surface 106.

Alternatively, device 100 can be equipped with a motorized or adjustable lift that allows the source 104 to be raised or lowered relative to the surface 106. Such an adjustment is preferably performed automatically in response to a signal from the controller 130. In accordance with this embodiment of the invention, UV dosages applied to the surface 106 can be maintained substantially constant by lowering the source 104 as the device travels faster across the surface 106, and raising the source 104 as the device 100 travels slower over the surface 106.

The sanitization device 100 can also include additional sources of UV radiation that operate under the control of controller 130. In accordance with one embodiment of the invention, a source of UV radiation 140 is provided that is configured to direct UV radiation onto the cleaning component 118 of the sanitization device 100, as illustrated in FIG. 1. When the cleaning component 118 is a rotatable scrubber, a rotatable sweeper, a squeegee (such as squeegee 119), or other cleaning component, the applied UV radiation operates to sanitize the cleaning component 118 thereby reducing the microorganism population on the component 118 and the emission of odors.

In accordance with another embodiment of the invention, a source of UV radiation 142 is positioned within a tank or waste container 144 of the sanitization device 100, in which waste, such as soiled cleaning solution or debris, is collected.

The source 142 operates to transmit UV radiation into the tank 144 to at least partially sanitized material collected therein.

As explained above, sanitization device 100 can operate as a surface cleaner, such as a carpet cleaner, a hard floor surface cleaner, or a street cleaner. Accordingly, sanitization device 100 can include a vacuum 146 that is used to facilitate the collection of soiled cleaning solution and debris from the surface 106. In operation, air is sucked into the device 100 at a collection location through an air intake 148 and the air is discharged through an exhaust 150 along with the collected waste material into the tank 144. In accordance with one embodiment of the invention, a source of UV radiation 152 is positioned to transmit UV radiation within the channel 154 through which the air travels before being exhausted, as illustrated in FIG. 1. The exposure of the air travelling in the channel 154 to the UV radiation operates to sanitize the air prior to its discharge. Alternatively, the source 142 in the waste container 144 can be positioned to expose the air and waste discharged through exhaust 150 to UV radiation to thereby eliminate the need for source 152.

More specific examples of the present invention that include many of the embodiments discussed above, will be provided with reference to FIGS. 2-9. Elements in the figures that are labeled similarly to the elements of FIG. 1 identify the same or similar elements.

Hard Floor Surface Cleaner

Figure 2:
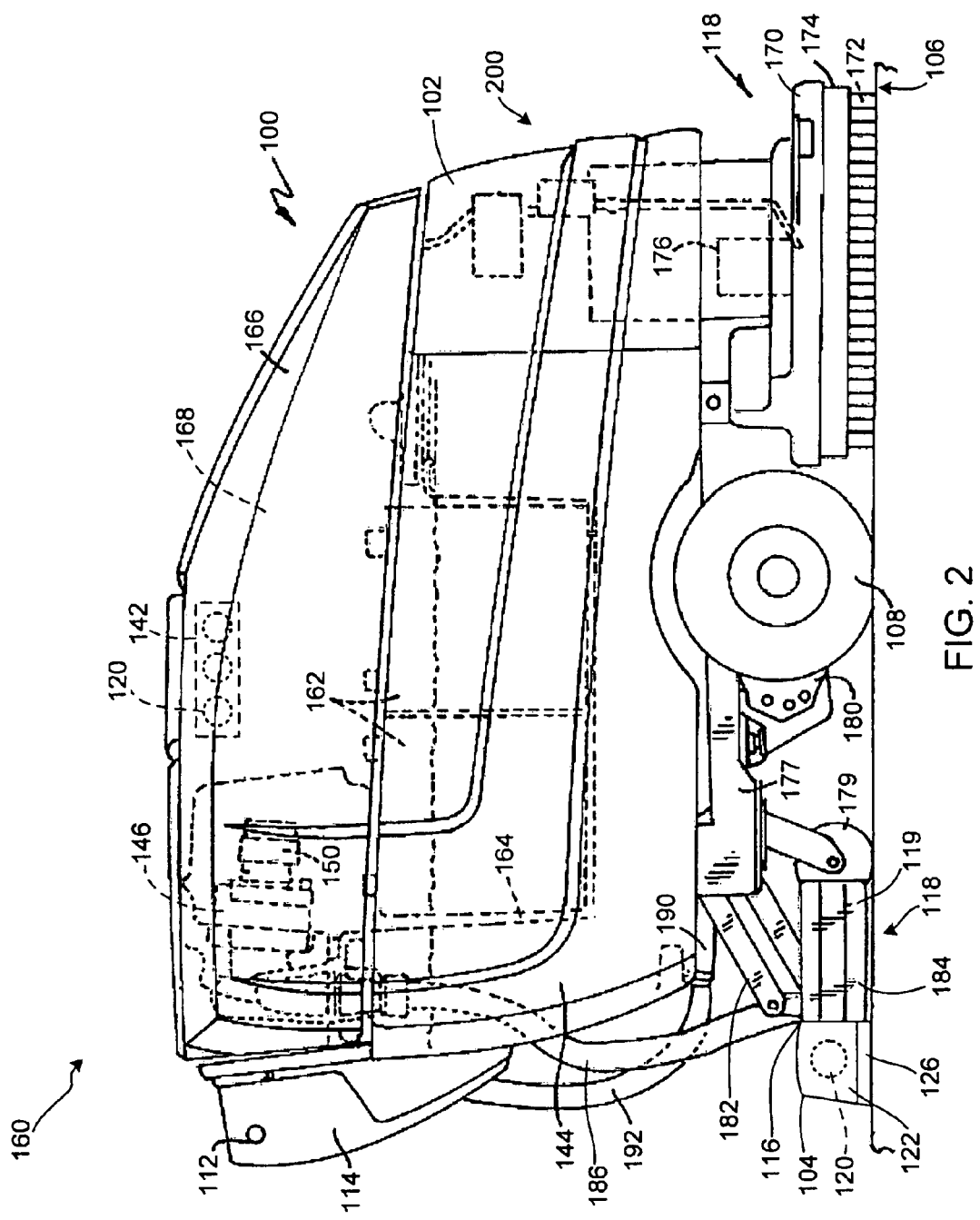
FIG. 2 is a side view of a sanitization device in the form of a hard floor surface cleaner in accordance with embodiments of the invention.

FIG. 2 illustrates a sanitization device 100 in the form of a hard floor surface cleaner 160 in accordance with embodiments of the invention. The illustrated sanitization device 100 is a walk-behind surface cleaner used to clean hard floor surfaces, such as concrete, tile, vinyl, terrazzo, etc. Alternatively, the cleaner 160 can be configured as a ride-on or towed-behind cleaner that performs in a similar manner as the depicted cleaner 160.

Cleaner 160 may include electrical motors powered through an on-board power supply 132, such as batteries 162 in battery compartment 164 or through an electrical cord. Cleaner 160 also includes a recovery tank 144 and a lid 166 attached along one side of the recovery tank 144 by hinges (not shown) so that lid 166 can be pivoted up to provide access to the interior of tank 144. Cleaner 160 also includes a tank 168 for containing cleaning liquid or a primary liquid component that is applied to the hard floor surface 106 during cleaning operations.

A cleaning component 118 in the form of a scrub head 170 includes a scrubbing member 172, shrouds 174 and a scrubbing member drive 176. Scrubbing member 172 may include one or more brushes, such as bristle brushes, pads, covers, or other hard floor surface scrubbing elements. Drive 176 includes one or more electric motors to rotate the scrubbing member 172. Scrubbing member 172 may be a disc type scrub brush rotating about a generally vertical axis of rotation relative to the surface 106. Alternatively, scrubbing member 172 may be a cylindrical type scrub brush rotating about a generally horizontal axis of rotation relative to the surface 106. Drive 176 may also oscillate scrubbing member 172. Scrub 170 is preferably attached to the mobile body 102 of cleaner 160 such that the scrub head 170 can be moved between a lowered cleaning position and a raised traveling position.

The mobile body 102 of cleaner 160 includes a frame 177 that supports recovery tank 144 on wheels 108 and castors 179. Wheels 108 are preferably driven by a motor and transaxle assembly shown schematically at 180. The rear of the frame 177 carries a linkage 182, to which a fluid recovery device 184 is attached. The linkage 182 allows the fluid recovery device 184 to be raised and lowered as desired. One embodiment of the fluid recovery device 184 includes a squeegee 119, as shown in FIGS. 1 and 2, which can also be considered a cleaning component 118. The vacuum 146 sucks the waste collected by squeegee 119 through a hose 186 and discharges the collected waste through the exhaust 150 and into an inlet chamber of the recovery tank 144. The bottom of the inlet chamber is provided with a drain 190 with a drain hose 192 connected to it.

One embodiment of cleaner 160 includes a cleaning liquid dispensing system 200 that is configured to dispense cleaning liquid to the surface 106 and/or scrub head 170. In accordance with one embodiment of the invention, the cleaning liquid dispensing system 200 is configured to generate a foamed cleaning liquid. Examples of such cleaning liquid dispensing systems are described in U.S. Pat. Nos. 6,585,827, 6,671,925, and 6,705,332, which are assigned to Tennant Company of Minneapolis, Minn.

As discussed above with regard to FIG. 1, cleaner 160 may include one or more sources of UV radiation. One UV source 104 is preferably mounted to the mobile body 102 at a rear side 116 of the frame supporting the squeegee 119 through an appropriate connection. As discussed above, the UV source 104 can include a housing 122 that shrouds the UV source 104 and includes an open bottom to allow the UV source 104 to expose the surface 106. Additionally, a flexible skirt 126 can extend from a bottom side of the housing 122 for engagement with the surface 106 to prevent leakage of UV radiation, when the linkage 182 is in a lowered position.

In accordance with another embodiment of the invention, a source of UV radiation 142 is configured to transmit UV radiation into the tank 144. The source 142 can be mounted inside the tank 144 on a top side of the lid 166, as shown, or in another suitable location within tank 144. Alternatively, the source 142 can be mounted outside of the tank 144 and configured to direct the UV radiation inside the tank 144 through a suitable window. Preferably, the source 142 is deactivated when the cover of the tank 144 is opened using an appropriate switch.

In accordance with yet another embodiment of the invention, the cleaner 160 may also include UV radiation sources 140 and 152 that are configured to apply UV radiation to the scrub head 170 and the air and waste material collected by the vacuum 146, respectively, as illustrated in FIG. 1.

In operation, the squeegee 119 and the source 104, shown in FIG. 2, are lowered to the surface 106 through actuation of the linkage 182. Next, the cleaning liquid dispensing system 200, the scrub head 170, the fluid recovery system 184, and one or more of the UV sources including source 104, are activated. The cleaner 160 is preferably driven by powered wheels 108 over the surface 106 in a forward direction as opposite the operator interface 114. As the cleaner 160 moves across the surface 106, the scrub head 170 scrubs the surface 106 with the cleaning liquid applied thereon. The soiled cleaning liquid is collected by the squeegee 119 and sucked into the tank 144 through the hose 186 by the vacuum 146 and is discharged into the tank 144 through the exhaust 150. The substantially cleaning liquid-free surface 106 that remains at the rear side 116 of the squeegee 119 is sanitized by the source 104 through the application of a suitable dosage of UV radiation, preferably in a range of 10-60 mW/cm$^2$, as the cleaner 160 moves across the surface 106.

Additionally, the soiled cleaning liquid collected into tank 144 can also be sanitized through application of an appropriate dosage of UV radiation produced by the source 142. The source 142 also preferably operates to sanitize the air and soiled cleaning liquid as it is discharged into the tank 144 by the vacuum 146, thus performing the function of source 152 shown in FIG. 1. Furthermore, another UV source 140 can direct UV radiation onto the rotating scrub head 170 to sanitize the scrub head 170 including the scrubbing member 172.

Floor Sweeper

Figure 3:
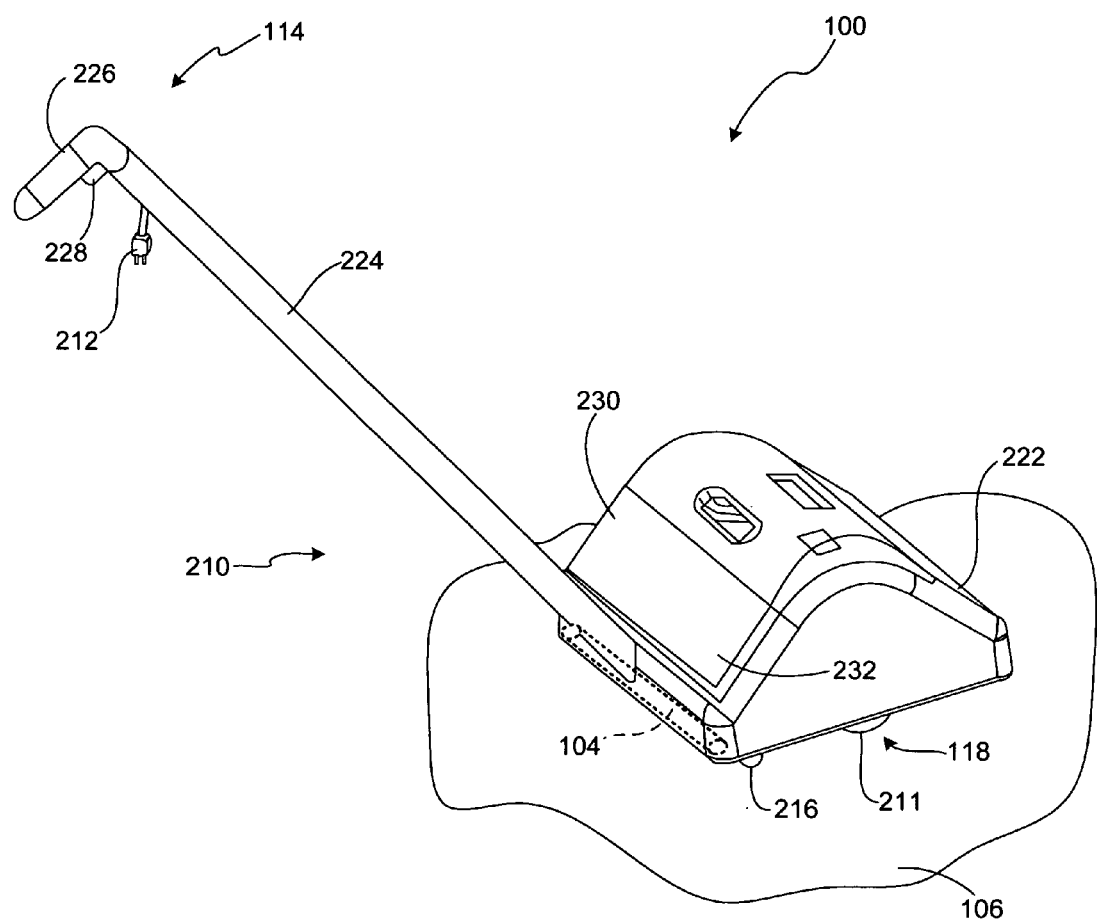
FIGS. 3 and 4 effectively show perspective and bottom plan views of a sanitization device in the form of floor sweeper in accordance with embodiments of the invention.
Figure 4:
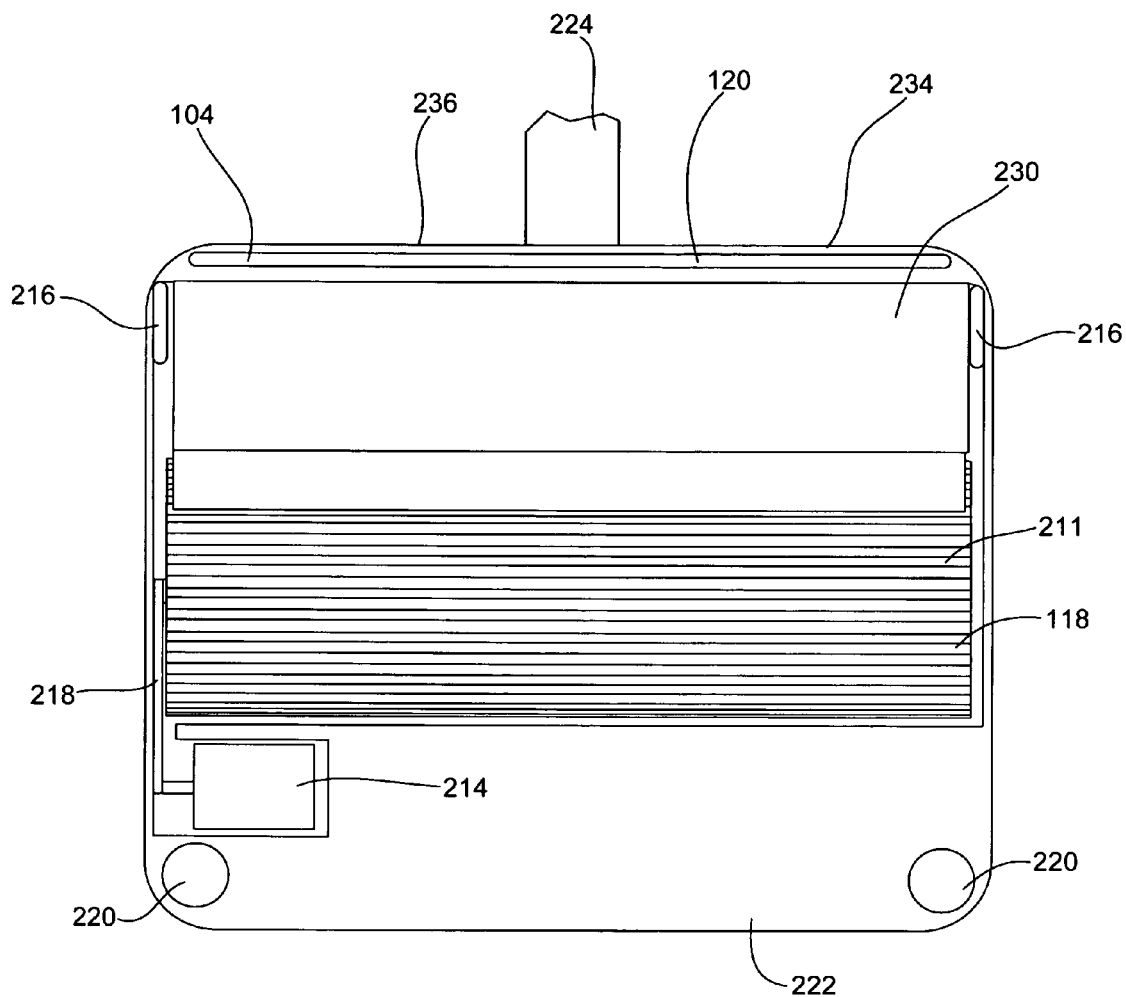

FIGS. 3 and 4 show a perspective view and a bottom plan view of the sanitization device 100 of the present invention in the form of a floor sweeper 210. Floor sweeper 210 is a walk-behind sweeper that includes a cleaning component 118 in the form of a rotatable sweeper 211 that is configured to sweep debris from hard floor surfaces, such as surface 106. Floor sweeper 210 can include an on-board power supply 132 (FIG. 1), such as a battery or be powered through a cord connected to plug 212. In accordance with one embodiment of the invention, floor sweeper 210 includes a motor 214 (FIG. 4) that drives support wheels 216 and the rotatable sweeper 211 through an appropriate connection 218. Rollers 220, formed of balls in sockets, are positioned at a front portion 222 of the sweeper 210 and support the sweeper 210 for turning movement along surface 106. The operator interface 114 of sweeper 210 includes a shaft 224 and a handle 226, at which an on-off switch 228 is preferably located.

The rotatable sweeper 211 preferably rotates such at the portion engaging the surface 106 rotates toward the shaft 224 or away from the front side 222 in order to deliver debris to a waste container 230 that is positioned to the rear of the rotating sweeper 211. The sweeper 210 includes a removable cover 232 through which the container 230 can be accessed to remove the collected debris.

Floor sweeper 210 also includes a source of UV radiation 104 that is powered by an internal or an external power supply. The source 104 is preferably shrouded by a housing 234 to a rear side of the rotatable sweeper 211 and is configured to transmit UV radiation to the surface 106 through a bottom opening 236 (FIG. 4), as described above. The source 104 preferably operates as discussed above to provide the desired sanitizing dosage of UV radiation to the surface 106 during sweeping operations.

In accordance with additional embodiments of the invention, floor sweeper 210 includes UV sources that are configured to expose the rotatable sweeper 211 and the contents of the container 230 to UV radiation, as described above with reference to FIG. 1. In accordance with yet another embodiment of the invention, a sanitation device is formed as illustrated in FIGS. 3 and 4, but without the rotatable sweeper 211. The resulting sanitation device 100 operates with the source 104 to provide a purely surface sanitizing function.

Street Sweeper

Figure 5:
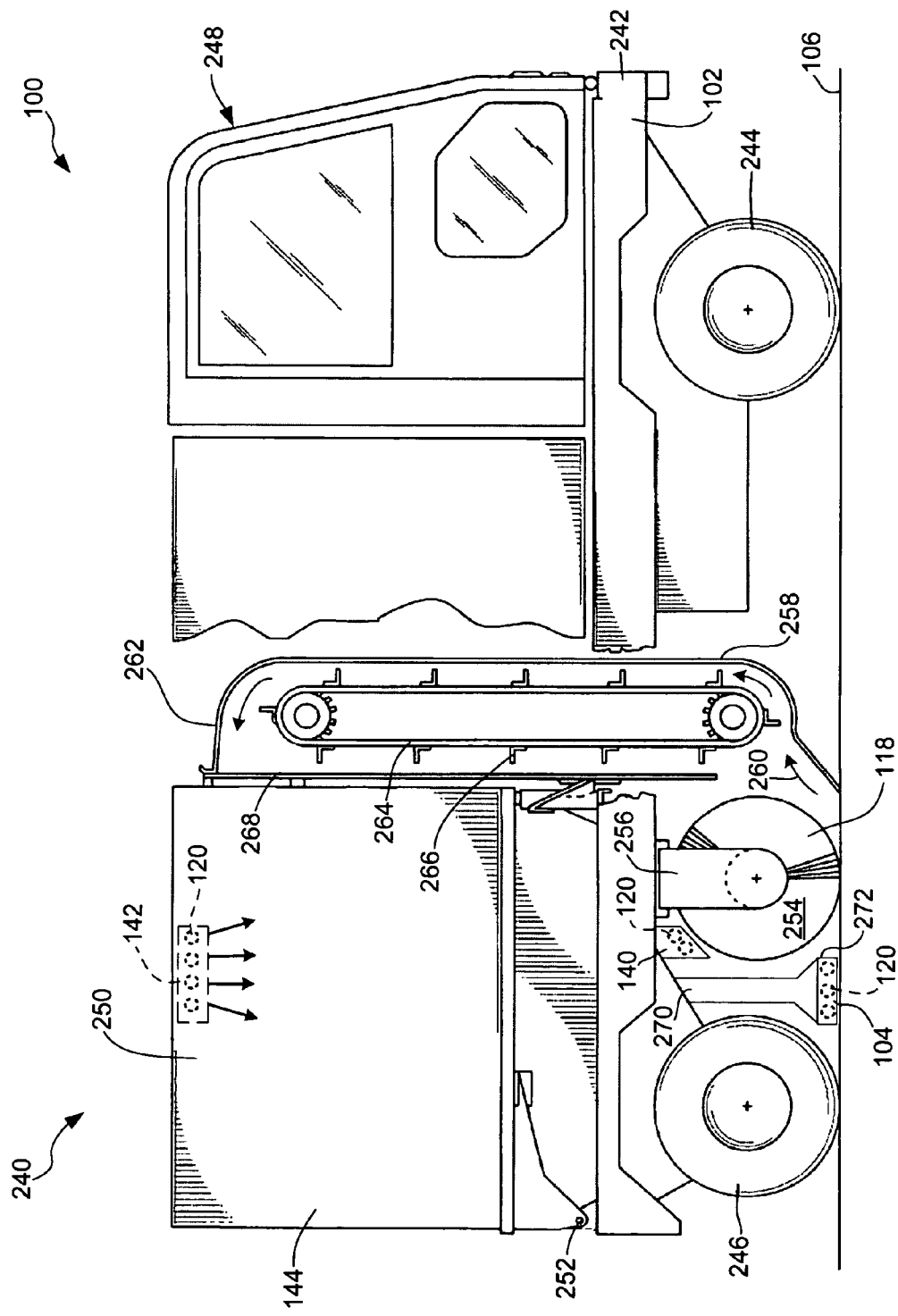
FIG. 5 is a side view of a sanitization device in the form of a street sweeper with portions broken away, in accordance with embodiments of the invention.

FIG. 5 shows a side view of a sanitation device 100 of the present invention in the form of a street sweeper 240 with portions broken away. The street sweeper 240 is principally used to clean streets, parking lots and similar outdoor areas, but is also used to clean large in-door industrial areas. The sweeper 240 includes a mobile body 102 that includes a frame 242 that is supported on front wheels 244 and rear wheels 246. A driver's cab 248 provides an operator interface where the vehicle operator has all of the customary controls for operating the sweeper 240.

The sweeper 240 also includes a waste container 250, which can be pivoted at a hinge 252 between the lowered operating position (shown) and a raised non-operating position. Sweeper 240 includes a cleaning component 118 in the form of a generally cylindrical sweeping brush 254 that is mounted on spaced supports 256 and extends generally transverse of the frame 242 and substantially across the width of the sweeper 240. Debris swept by the sweeper brush 254 is directed into a conveyor 258, as indicated by the arrow 260.

The conveyor 258 has an enclosure 262, within which is contained a flexible drive member 264 and a series of spaced paddles 266. When the conveyor is operated, the debris swept by the brush 254 is picked up by the paddles 266 and raised to the upper end of the conveyor enclosure 262 where it is deposited in the container 250 through aligned openings 268 in container 250.

Sweeper 240 also includes at least one source of UV radiation, such as source 104 that is mounted to frame 242 by a suitable support member 270. Source 104 is powered by an on-board power supply of the sweeper 240. The source 104 is preferably shrouded by a housing 272, as described above, and transmits UV radiation substantially across the width of the sweeper 240 to the surface 106 during sweeping and/or non-sweeping operations.

In accordance with another embodiment of the invention, sweeper 240 includes a second source of UV radiation 140 mounted to frame 242 and configured to expose the brush 254 to UV radiation during rotation of the brush 254. As a result, source 140 operates to sanitize the brush 254 during sweeping operations.

Another embodiment of sweeper 240 includes a source of UV radiation 142 that is configured to direct UV radiation into the waste container 250. The UV radiation produced by source 142 operates to sanitize the debris collected in container 250.

Handheld Sanitation Device

Figure 6:
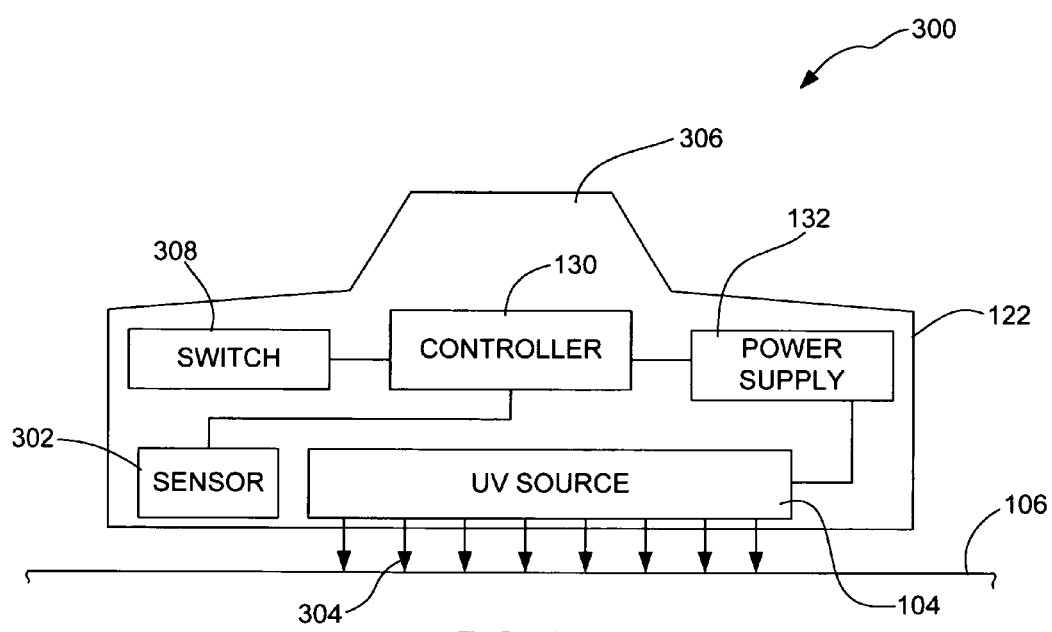
FIG. 6 is a simplified diagram of a handheld sanitization device, in accordance with embodiments of the invention.

FIG. 6 is a simplified diagram of a sanitization device 300 that is generally configured for handheld operation in accordance with embodiments of the invention. A more detailed example of sanitation device 300 is provided in FIGS. 7 and 8, which are side and bottom plan views, respectively.

Sanitation device 300 includes many of the components described above with reference to sanitation device 100 and are labeled accordingly.

In general, sanitation device 300 includes a housing 122, a source of UV radiation 104, and a sensor 302. Housing 122 of sanitation device 300 preferably includes a handle 306 to allow a user of the device 300 to move the device 300 across the surface 106 by hand. The housing 122 preferably shrouds the UV source 104 (i.e., blocks the UV radiation) except at the open bottom, as described above. Additionally housing 122 can include a flexible skirt that surrounds the perimeter of the bottom opening and extends toward the surface 106 for engagement therewith during sanitizing operations to prevent leakage of UV radiation, as discussed above. Housing 122 preferably contains a power supply 132. Alternatively, sanitation device 300 can receive power through a cord.

One embodiment of sanitization device 300 includes a controller 130 that is configured to control the operations of device 300 including the supplying of power to source 104 and receiving signals from sensor 302. A main switch 308 can also be provided on housing 122 that provides a signal to controller 130 to enable operation of the sanitization device 300.

Sanitization device 300 can have one or more sensors 302. Each sensor 302 operates to detect when the source 104 is within a predetermined distance from the surface 106. When the source 104 is positioned within the predetermined from surface 106, sensor 302 provides a signal to the controller 130 indicating such. The controller can then enables power to activate the source 104. In this manner, operation of sanitization device 300 can be prevented when the source 104 is positioned outside the predetermined distance from the surface 106 to thereby prevent inadvertent exposure to UV radiation.

The sensors 302 can take on many different forms. For example, sensors 302 can be mechanical switches, capacitance sensors and any other suitable sensor that can be used to detect a proximity of the surface 106 to the source 104. In accordance with one embodiment of the invention, the sensors 302 include a retractable component, such as a wheel or a support foot which retracts as the device 300 is pressed against the surface 106. When the threshold distance is reached, the retractable component closes a switch or otherwise signals the controller 130 to enable power to the source 104.

Figure 9:
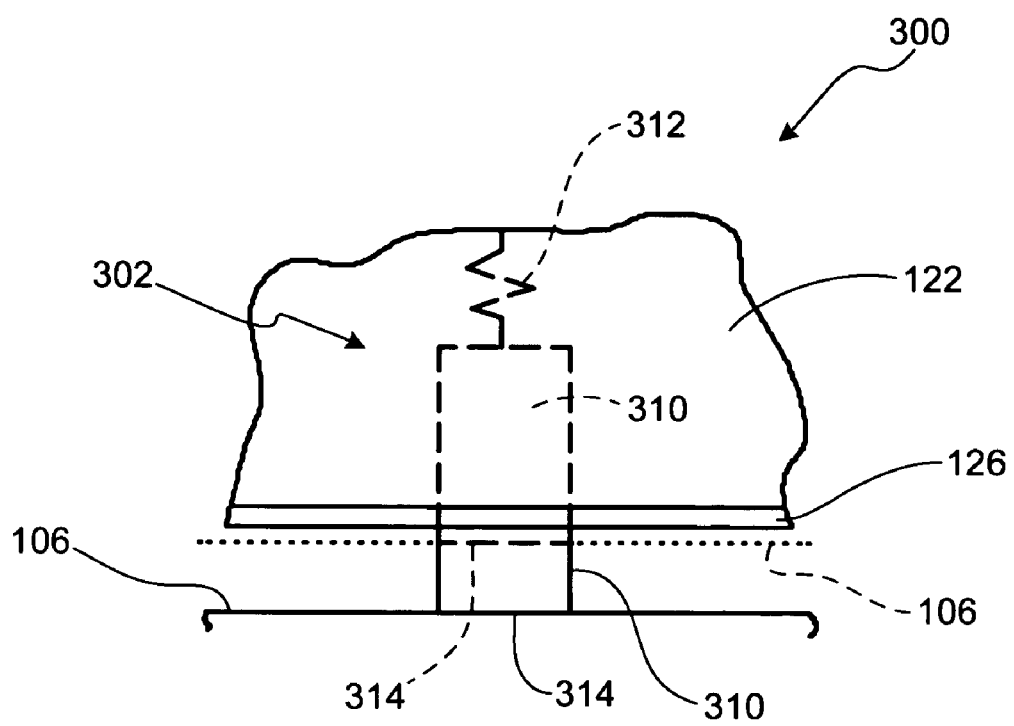
FIG. 9 is a side view of a portion of a handheld sanitization device illustrating a sensor, in accordance with embodiments of the invention.

An example of this type of sensor 302 is illustrated in FIG. 9. In accordance with this embodiment of the invention, a support foot 310 extends from a bottom of the housing 122 and is biased toward an extended position, as indicated by the solid line in FIG. 9, by a suitable biasing component, such as a spring 312, when sanitization device 300 is displaced from surface 106 a distance that exceeds the predetermined threshold distance. As UV source 104 is brought closer to surface 106, pressure applied to a bottom surface 314 of the foot 310 by the surface 106 causes the foot 310 to move toward a retracted position, as illustrated in phantom in FIG. 9. The movement of the foot 310 toward the retracted position eventually closes a switch, or otherwise causes a signal to be sent to the controller 130 that indicates that the source 104 is within the predetermined distance from surface 106. Controller 130 can then enable power to the UV source 104 thereby causing UV source 104 to produce UV radiation, which is directed to the surface 106. Once the sanitization operation of the surface 106 is completed, power to the UV source 104 can be disabled through actuation of the main switch 308 (FIG. 6), or by displacing UV source 104 from the surface 106 a distance that exceeds the predetermined threshold distance and causes the foot 310 to return to the extended position.

Method of Using the Sanitation Device

Figure 10:
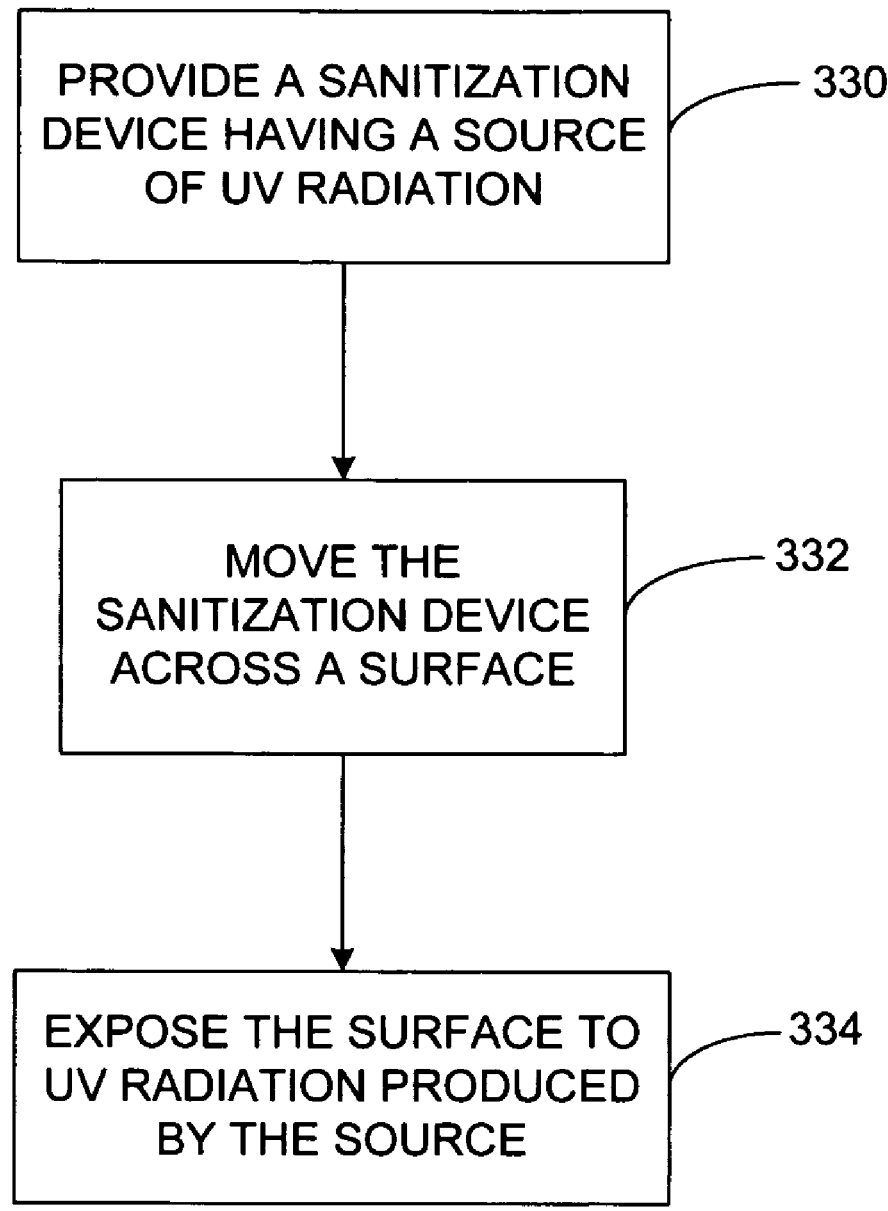
FIG. 10 is a flowchart illustrating a method of sanitizing a surface in accordance with embodiments of the invention.

Additional embodiments of the invention are directed to methods of using the sanitization devices 100 and 300 described above. The general method is illustrated in the flowchart of FIG. 10. At step 330, a sanitization device is provided having a source of UV radiation. Next, at step 332, the sanitization device is moved across a surface. Finally, the surface is exposed to UV radiation produced by the source at step 334.

Embodiments of step 330 include providing the various embodiments of sanitization devices 100 and 300 described above. For instance, one embodiment of step 330 includes providing a sanitization device, such as sanitization device 100 or sanitization device 300 described above, that includes a source 104 of UV radiation. In accordance with another embodiment of step 330, the sanitization device includes a mobile body 102 that is configured to travel across the surface 106, a surface cleaning component 118 configured to engage the surface 106, and a source 104 of UV radiation that is mounted to the mobile body 102 such as the sanitization device 100 described above.

Figure 7:
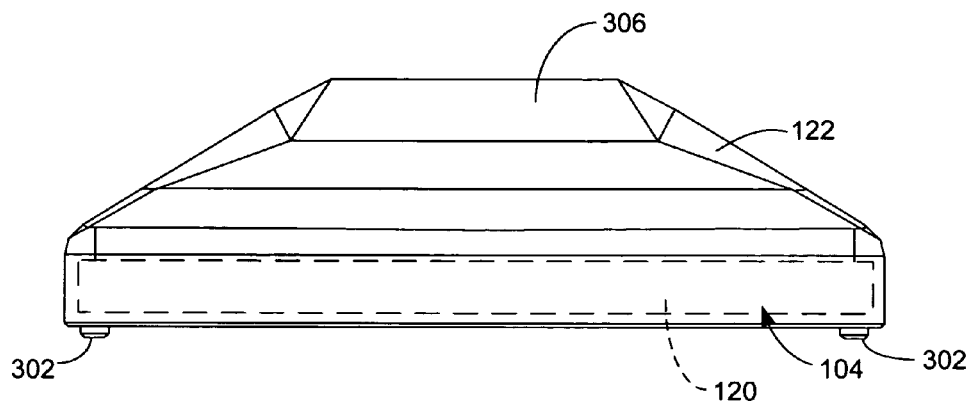
FIGS. 7 and 8 respectively are side and bottom plan views of a handheld sanitization device, in accordance with embodiments of the invention.
Figure 8:
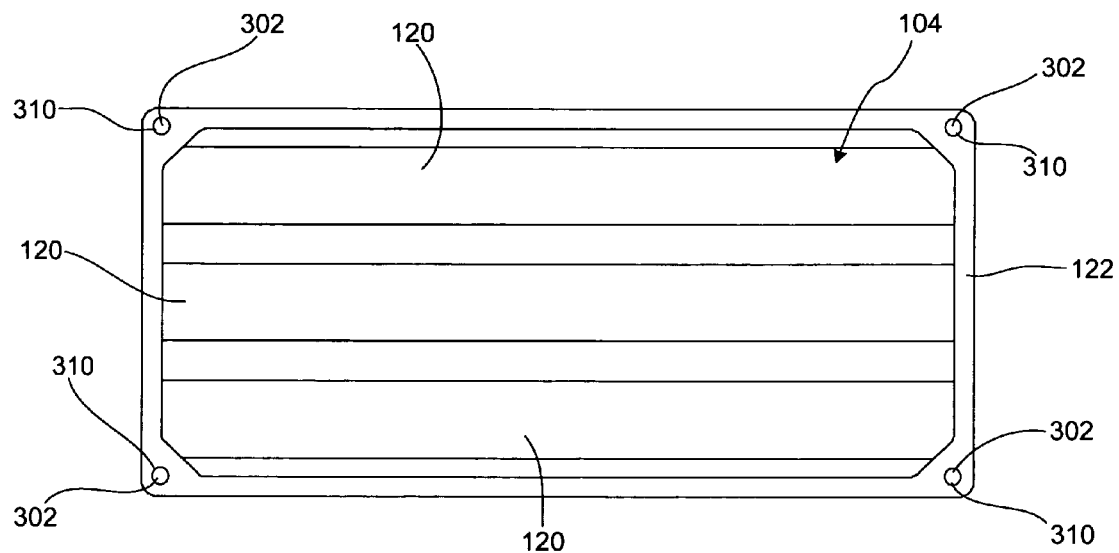

Embodiments of step 332 include moving the sanitization device (100 or 300) by hand across the surface 106; moving the sanitization device across the surface 106 on non-powered and power-driven wheels, such as wheels 108 (FIGS. 1 and 2), wheels 216 (FIGS. 3 and 4), and wheels 244 and 246 (FIG. 5); or sliding the sanitization device across the surface 106 on, for example, slidable feet 310 (FIGS. 7 and 8).

Embodiments of step 334 include exposing the surface 106 to a dosage of UV radiation of less than 60 mW/cm$^2$, or other dosage of UV radiation that provides the desired sanitization of the surface 106.

Method of Sanitizing Components of a Cleaner

Another aspect of the present invention is directed to methods of sanitizing components of a mobile surface cleaner. Examples of such mobile surface cleaners include cleaner 160 (FIG. 2), cleaner 210 (FIGS. 3 and 4), and cleaner 240 (FIG. 5) that include a component such as a cleaning component 118 or a waste container or tank 144. The mobile surface cleaner generally includes a mobile body 102 and a source of UV radiation, such as source 140 or source 142, shown in FIG. 1.

In the method, a source 140 is positioned to expose the cleaning component 118, or a source 142 is positioned to expose the interior of the waste container or tank 144, as shown in FIGS. 1, 2, and 5. Next, the cleaning component 118 or the interior of the waste container or tank 144 is exposed to UV radiation produced by the source 104. The exposure of the cleaning component 118 and the interior of the waste container or tank 144, operates to control the proliferation of microorganisms and the generation of odor.

Although the present invention has been described with reference to preferred embodiments, workers skilled in the art will recognize that changes may be made in form and detail without departing from the spirit and scope of the invention.

What is claimed is:

1. A sanitization device comprising:
    a mobile body configured to travel over a surface;
    a cleaning liquid dispensing system supported on the mobile body and configured to dispense a cleaning liquid to the surface;
    a squeegee coupled to a rear side of the mobile body and configured to engage the surface;
    a rotatable scrubber mounted to the mobile body and configured to scrub the surface;
    a source of UV radiation attached to the mobile body and positioned at a rear side of the squeegee, the source of UV radiation configured to direct UV radiation to the surface;
    a tank mounted to the mobile body; and
    a vacuum supported by the mobile body and configured to remove liquid from the surface that is collected by the squeegee and deposit the liquid into the tank.

2. The device of claim 1, further comprising a second source of UV radiation configured to direct the UV radiation onto the rotatable scrubber.

3. The device of claim 1, further comprising a second source of UV radiation configured to direct UV radiation into the tank.

4. The device of claim 1, wherein the UV radiation has a wavelength of less than 280 nm.

5. The device of claim 1, wherein a power consumption of the source automatically varies in accordance with a speed at which the mobile body travels.

6. The device of claim 1 including a shroud covering sides of the source that do not face the surface.

7. The device of claim 1, wherein the source is configured to direct a dosage of UV radiation to the surface of less than 60 mW/cm$^2$.

* * * * *